(12) United States Patent
Nioutsikou

(10) Patent No.: US 9,364,186 B2
(45) Date of Patent: Jun. 14, 2016

(54) DOSE RECONSTRUCTION DURING RADIATION THERAPY

(71) Applicant: Elena Nioutsikou, Gif sur Yvette (DE)

(72) Inventor: Elena Nioutsikou, Gif sur Yvette (DE)

(73) Assignee: Siemens Aktiengesellschaft, München (DE)

( * ) Notice: Subject to any disclaimer, the term of this patent is extended or adjusted under 35 U.S.C. 154(b) by 593 days.

(21) Appl. No.: 13/667,835

(22) Filed: Nov. 2, 2012

(65) Prior Publication Data

US 2013/0114784 A1 May 9, 2013

(30) Foreign Application Priority Data

Nov. 4, 2011 (DE) .......................... 10 2011 085 773

(51) Int. Cl.
*A61N 5/10* (2006.01)
*A61B 6/00* (2006.01)
*A61B 6/03* (2006.01)

(52) U.S. Cl.
CPC ............... *A61B 6/4208* (2013.01); *A61B 6/032* (2013.01); *A61B 6/4258* (2013.01); *A61B 6/4266* (2013.01); *A61B 6/4417* (2013.01); *A61B 6/5235* (2013.01); *A61N 5/1038* (2013.01); *A61N 2005/1054* (2013.01); *A61N 2005/1061* (2013.01)

(58) Field of Classification Search
CPC .. A61B 6/4208; A61B 6/4258; A61B 6/4266; A61B 6/5235; A61B 6/4417; A61B 6/032; A61N 5/1038; A61N 2005/1054; A61N 2005/1061

USPC ............................................................ 378/65
See application file for complete search history.

(56) References Cited

U.S. PATENT DOCUMENTS 8,073,104 B2 * 12/2011 Yan ...................... A61N 5/1049
378/65

(Continued)

OTHER PUBLICATIONS

German Office Action dated Oct. 22, 2012 for corresponding German Patent Application No. DE 10 2011 085 773.7 with English translation.

(Continued)

*Primary Examiner* — Michael Maskell
(74) *Attorney, Agent, or Firm* — Lempia Summerfield Katz LLC

(57) ABSTRACT

A method for the reconstruction of a dose administered in an object to be irradiated includes providing a radiation therapy device. The radiation therapy device includes a therapeutic radiation source for emitting a therapeutic treatment beam, a portal detector opposing the therapeutic radiation source for recording measurement data of the treatment beam once the therapeutic radiation source has left the object to be irradiated, and a single or multi slice computed tomography scanner having a kV x-ray source and an opposing kV detector for producing a computed tomography of the object positioned in the radiation therapy device. The method also includes recording a computed tomography image of the object to be irradiated with the computed tomography scanner, and using the computed tomography image in order to reconstruct a dose administered to the object from measurement data of the portal detector.

20 Claims, 2 Drawing Sheets

(56) References Cited

U.S. PATENT DOCUMENTS

| | | | |
|---|---|---|---|
| 2004/0096033 A1 | 5/2004 | Seppi et al. | |
| 2006/0098856 A1* | 5/2006 | Botterweck | A61B 6/032 382/131 |
| 2007/0058778 A1 | 3/2007 | Coleman et al. | |
| 2007/0280408 A1* | 12/2007 | Zhang | A61B 6/025 378/10 |
| 2008/0091388 A1* | 4/2008 | Failla | A61N 5/1031 703/2 |
| 2009/0175418 A1 | 7/2009 | Sakurai et al. | |
| 2010/0119032 A1* | 5/2010 | Yan | A61N 5/1049 378/4 |
| 2012/0140887 A1* | 6/2012 | Mundy | A61N 5/1048 378/65 |

OTHER PUBLICATIONS

V.N. Hansen et al., "The Application of Transit Dosimetry to Precision Radiotherapy," Med. Phys., vol. 23, No. 5, pp. 713-721 (1996).

M. Partridge et al., "IMRT Verification by Three-dimensional Dose Reconstruction from Portal Beam Measurements," Med Phys., vol. 29, No. 8, pp. 1847-1858 (2002).

W. Van Elmpt, et al., "A Literature Review of Electronic Portal Imaging for Radiotherapy Dosimetry," Radiotherapy and Oncology, vol. 88, No. 3, pp. 289-309 (2008).

J. Chen, et al., "Dose-guided Radiation Therapy with Megavoltage Cone Beam CT," BJR, pp. 87-98 (2006).

* cited by examiner

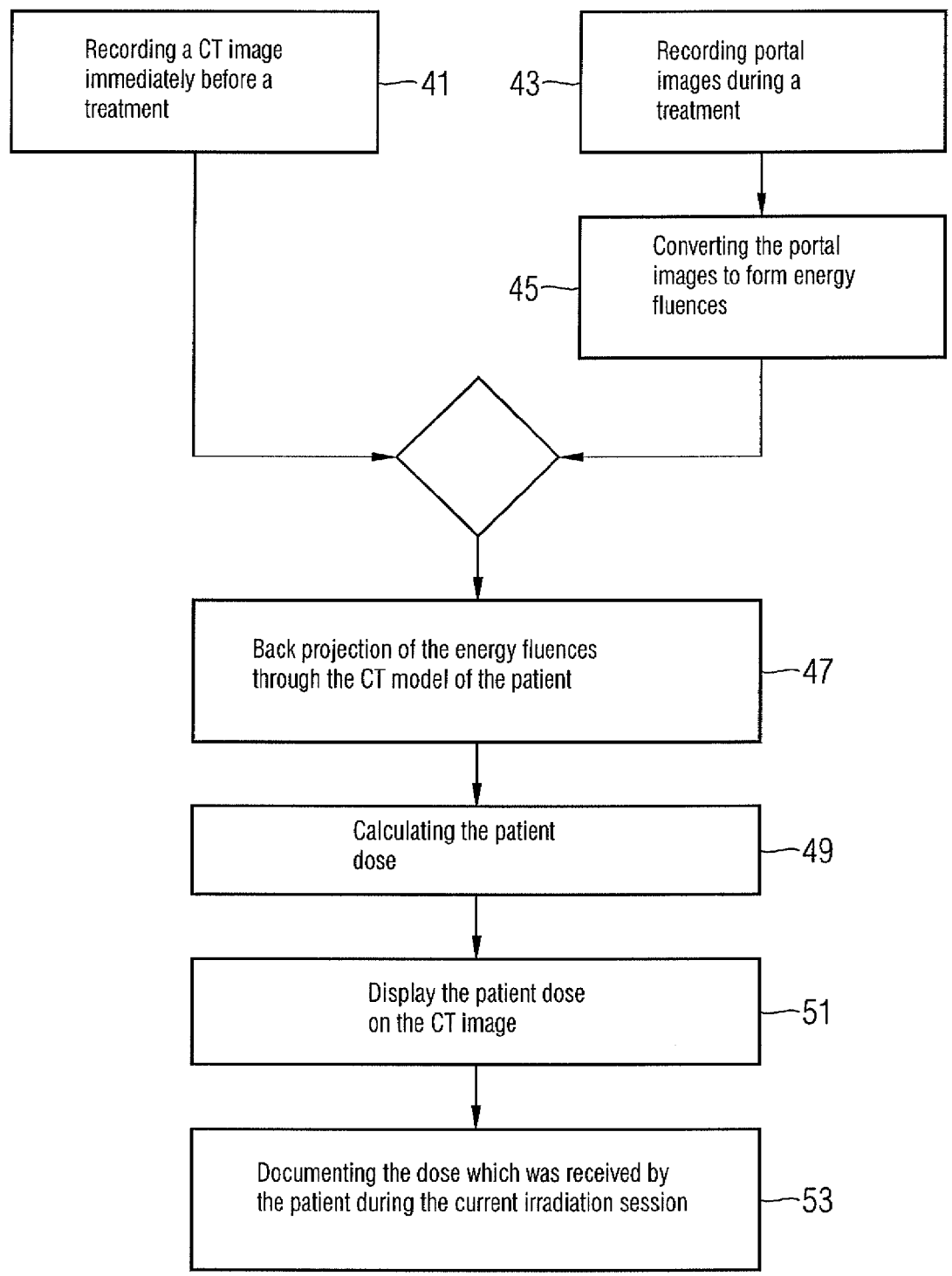

DOSE RECONSTRUCTION DURING RADIATION THERAPY

This application claims the benefit of DE 10 2011 085 773.7, filed on Nov. 4, 2011.

BACKGROUND

The present embodiments relate to a method for the reconstruction of a dose administered to a patient within the scope of radiation therapy using an external radiation source and a correspondingly embodied radiation therapy device.

Radiation therapy is an established method, in which ionizing radiation is used in order to treat pathological tissue such as tumor tissue, for example. The aim of radiation therapy is to irradiate the tissue to be treated with an adequate therapeutic dose and in the process, simultaneously to protect healthy, surrounding tissue. The therapeutic effect is based, for example, on ionizing radiation having a different effect on healthy and pathological tissue.

Within the scope of radiation therapy, the dosimetry and dose calculation deal, for example, with the problem of how much dose has actually been applied to the patient during the course of a radiation therapy treatment using an external radiation source. Different variables may be calculated in this process (e.g., the dose applied at a specific point through to the 3D dose distribution).

US 2007/0058778 A1 discloses a method for dose-controlled radiation therapy.

SUMMARY AND DESCRIPTION

The present embodiments may obviate one or more of the drawbacks or limitations in the related art. For example, a method that allows the dose applied to an object to be irradiated, to be determined precisely and with little effort is provided.

In one embodiment of a method for the reconstruction of a dose administered to an object to be irradiated includes providing a radiation therapy device. The radiation therapy device includes a therapeutic radiation source for outputting a therapeutic treatment beam, and a portal detector opposing the therapeutic radiation source for recording measurement data of the treatment beam once the treatment beam has left the object to be irradiated. The radiation therapy device also includes a single or multi slice computed tomography scanner. The single or multi slice computed tomography scanner also includes a kV x-ray source and an opposing kV detector for producing a computed tomograph of the object positioned in the radiation therapy device. The method includes recording a computed tomography image of the object to be irradiated with the computed tomography scanner, and using the computed tomography image to reconstruct a dose applied to the object from measurement data of the portal detector.

The method is implemented in conjunction with a radiation therapy device that has a portal detector and a computed tomography scanner.

The detector allows the treatment beam to be detected once the treatment beam has penetrated the object to be irradiated (e.g., a patient or a phantom). Since the detector detects the therapeutic beam in the treatment beam direction, the detector is also referred to as portal detector.

For example, a two-dimensional flat-panel detector may be used as a portal detector (e.g., an electronic portal imaging device (EPID)).

The computed tomography scanner used in the radiation therapy device is a conventional single or multi slice computed tomography scanner that, in contrast to cone beam computed tomography scanners, uses a single or multi slice kV detector and may use a fan-type beam, for example. In order to record the measurement data, the kV x-ray source and the kV x-ray detector are rotated numerous times around the object to be imaged, compared to the cone beam computed tomograph scanner, with which a single rotation may already be sufficient to record the raw image data for a 3D reconstruction of the image. For example, a spiral CT (e.g., CT for computed tomograph and/or computed tomography) may be used.

With the computed tomography scanner, the current transmission factors of the object to be irradiated may be determined. This information is used to convert the measurements of the portal detector into the dose that has also actually been administered to the object irradiated by the treatment beam. The dose that the patient actually receives during a fraction of a radiation therapy treatment and also during the course of the entire treatment may therefore be measured and documented.

Contrary to methods, in which there is recourse to a planning CT in order to obtain information about the anatomy of the patient, the computed tomography scanner of the radiation therapy device allows the anatomy of the patient to be imaged immediately before (or even during) the recording of the measurement data with the portal detector (e.g., in the same treatment fraction immediately before the start of the irradiation or during the irradiation). The data relating to the anatomy of the patient that is used for the dose reconstruction, for which the recorded computed tomography is then used, are recorded in a strict temporal context for radiation purposes and allow a more precise dose reconstruction.

Contrary to methods in which a cone beam CT image is used for dose reconstruction (e.g., an MV Cone Beam CT or a kV Cone Beam CT), the computed tomography image that has been recorded with a conventional computed tomography scanner allows the attenuation information required for the dose calculation to be determined more precisely and/or directly with the aid of the computed tomography image. The electron density information may therefore be obtained directly from the computed tomography image. Since a radiation planning and the dose calculation implemented in the process relate to a conventional planning CT, the same established standard may be used immediately in order to implement the dose reconstruction. A dose calculation within the scope of radiation therapy, which is based on a conventional computed tomography image, corresponds, for example, to the gold standard of radiation therapy.

By contrast, the information relating to the attenuation of the photons in the object may not be easily obtained from an MV cone beam CT or a kV cone beam CT of the object. Further acts (e.g., a return to the planning CT or an additional approximation of the electron density) may be necessary with the aid of the cone beam CT image, which complicates the dose reconstruction.

Therefore, with the method, the computed tomography image may be the sole image of the object, to which reference is made during the reconstruction of the dose administered to the object. For example, the planning CT may not be used. All measurements that are used to determine the administered dose are taken at the time of the treatment and are therefore current.

The publication by van Elmpt, W., et al., "A literature review of electronic portal imaging for radiotherapy dosimetry," Radiotherapy and Oncology 88, 2008, pp. 289-309, discloses methods as to how a dose applied to the object may be calculated from the measurement values recorded with the portal detector.

During the reconstruction of the dose administered to the object in a first act, for example, the measurement data of the portal detector may be converted into dose in water/dose to water. The portal detector may be calibrated in a preliminary method in order, as a result, to subsequently be able to calculate the dose in water/dose to water from the detector raw data.

In a second act, for example, the dose administered to the object is reconstructed from the dose in water/dose to water values. In an embodiment of the method, the computed tomography image is used in order to obtain information about how the photons in the object of the body are attenuated. The transmission values determined by the computed tomography scanner influence this reconstruction or conversion.

The raw data of the portal detector is converted to form primary energy fluence values. The measurement data of the detector, which characterize the applied treatment beam that passes through the object, are further processed, for example, by back projection of the current anatomy of the object, as may be determined with the aid of the current computed tomography scanner.

The method may also be used within the scope of rotation radiation therapy, in which the treatment beam is not applied from one or a number of fixed points, but instead rotates around the patient during the irradiation. The portal detector may also be rotated about a center of rotation. The measurement data recorded by the portal detector is assigned to the rotation positions, at which the measurement data has been recorded in each instance. The reconstruction of the administered dose may take place by using the rotation position assigned to the measurement data. For example, the recorded measurement data may be provided with a time stamp that identifies the angle of rotation, at which the recording has taken place in each instance.

The method may also be used in order to integrate the dose actually administered, which has been applied during more than one treatment fraction.

A computed tomography image may be recorded for a number of irradiation sessions in each instance. A reconstruction of the dose administered in the irradiation session takes place for each of the number of irradiation sessions respectively by using the computed tomography image recorded during this irradiation session. An applied dose cumulated during the course of the irradiation sessions is determined for a structure in the object.

The CT image allows, on account of the good visualization properties, the regions of interest (e.g., the target volume/s and/or the organls at risk) to be segmented. The information relating to the ROIs may be combined with the applied dose. The dose that has actually been applied in one of the ROIs may be determined in this way. During the course of the irradiation sessions, all this data may be registered to form a reference phase (e.g., about an elastic registration) in order thus to determine the dose that one of the regions of interest has received during the course of a number of fractions. The CT images may be registered to form a CT image of the reference phase.

One embodiment of a radiation therapy device for the treatment of an object to be irradiated and for the reconstruction of a dose administered to the object to be irradiated during the treatment includes a therapeutic radiation source for emitting a therapeutic treatment beam, and a portal detector opposing the therapeutic radiation source for recording measurement data of the treatment beam, after the treatment beam has left the object to be irradiated. The radiation therapy device also includes a single or multi slice computed tomography scanner having a kV x-ray source and an opposing kV detector for producing a computed tomograph of the object positioned in the radiation therapy device. The radiation therapy device includes a control apparatus that is configured to record a computed tomography image of the object to be irradiated with the computed tomography scanner during a treatment session, and for reconstructing the dose administered to the object from the measurement data of the portal detector using the computed tomography image.

During this process, the control apparatus controls the individual components of the radiation therapy device and collects data that is recorded by the computed tomography scanner and the portal detector during an irradiation session. The control apparatus processes the data and implements a method, as described above. The control apparatus may, for example, be implemented in one or more computer units that are connected to one another.

The preceding and the following description of the individual features, the advantages and the effects relate both to the apparatus and to the method, without this being mentioned in each case explicitly in detail. The individual features disclosed in the description may also be provided in combinations other than those shown.

BRIEF DESCRIPTION OF THE DRAWINGS

FIG. 2 shows a flowchart of one embodiment of a method for the reconstruction of a dose administered to an object to be irradiated.

DETAILED DESCRIPTION OF THE DRAWINGS

Figure 1:
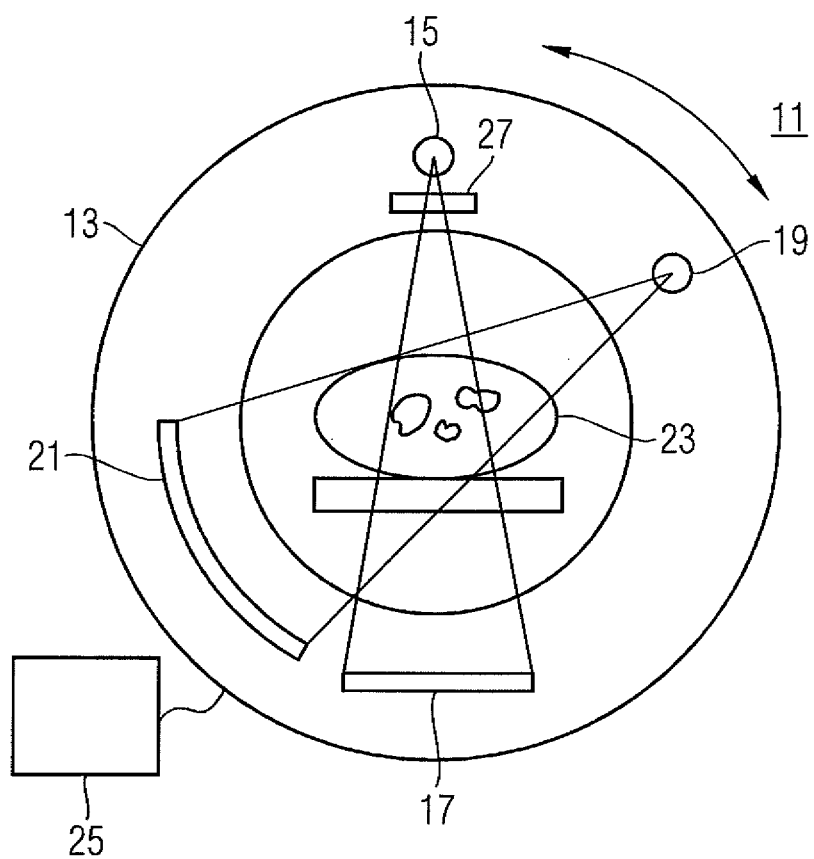
FIG. 1 shows one embodiment of a radiation therapy device.

FIG. 1 shows a highly schematic radiation therapy device 11 having an O-shaped gantry 13.

A therapeutic radiation source 15 is mounted in the gantry 13 so as to be rotatable. The therapeutic radiation source 15 faces an electronic portal imaging device (EPID) 17. A computed tomography scanner with a kV x-ray source 19 and a kV x-ray detector 21 is also integrated in the radiation therapy device 11.

A patient 23 is positioned in the center of the gantry for treatment and in order to record the CT image.

In this way, a control apparatus 25 controls the individual components of the radiation therapy device 11 and collects and processes data that is recorded by the computed tomography scanner and the EPID during an irradiation session.

A transmission detector 27 (e.g., a transmission flat panel) may optionally be arranged in the radiation therapy device 11 upstream of the patient 23 in the radiation path. The transmission detector 27 may be arranged, for example, in a beam head in the vicinity of the therapeutic radiation source 15. The distribution of energy fluence of the irradiation beam may be measured in real-time. Read-out data of the transmission detector 27 and of the EPID 17 may be compared with one another. The contribution of the object found in the radiation path (e.g., the patient 23) may be determined. The dose administered to the object 23 may then be reconstructed using the measurement data of the EPID 17 and of the transmission detector.

This embodiment is advantageous in that the treatment beam, such as is currently applied, is measured and taken into account, and not only the treatment beam, as was planned.

FIG. 2 shows a schematic diagram, as to how the dose applied during the course of an irradiation session may be reconstructed.

A CT image is recorded with a CT scanner immediately before the start of an irradiation session, the CT scanner being integrated in the radiation therapy device (act 41).

Portal images are recorded during the irradiation session (e.g., during the application of the treatment session) (act 43).

The portal images are converted to form energy fluences (act 45).

The CT image is used in order to backproject the energy fluences through the CT model (act 47) in order to calculate the dose administered to the patient (act 49).

Since the patient dose has been determined, the patient dose is shown on the CT image (act 51). The dose applied to the patient during the treatment session is documented (act 53).

By way of example, the dose thus documented may be used to determine a cumulated dose over a number of treatment sessions in a specific region.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for the reconstruction of a dose administered to an object to be irradiated, the method comprising:
   recording a computed tomography image of the object to be irradiated with a single or multi slice computed tomography scanner, the single or multi slice computed tomography scanner comprising a kV x-ray source and an opposite kV detector for producing a computed tomography of the object positioned in a radiation therapy device;
   recording measurement data of a therapeutic treatment beam with a radiation therapy device, the radiation therapy device comprising a therapeutic radiation source for emitting the therapeutic treatment beam and a portal detector opposing the therapeutic radiation source for recording measurement data of the treatment beam once the treatment beam has left the object to be irradiated, the measurement data including portal images recorded during treatment; and
   reconstructing the dose administered to the object from the portal images recorded during treatment and the computed tomography image, wherein the reconstructing comprises:
      converting the portal images to energy fluences; and
      backprojecting the energy fluences using the computed tomography image as a model.

2. The method as claimed in claim 1, further comprising:
   converting the measurement data of the portal detector into dose in water/dose to water values during the reconstruction of the dose administered to the object; and
   reconstructing the dose administered to the object from the dose in water/dose to water values using the computed tomography image.

3. The method as claimed in claim 1, further comprising:
   rotating the portal detector about a center of rotation; and
   assigning the measurement data recorded by the portal detector to rotation positions, at which the recording of the measurement data has taken place,
   wherein reconstructing the dose administered to the object comprises reconstructing the dose administered to the object using the rotation positions assigned to the measurement data.

4. The method as claimed in claim 1, wherein the computed tomography image is the only three dimensional (3D) image of the object that is used during the reconstruction of the dose administered to the object.

5. The method as claimed in claim 1, wherein recording the computed tomography image comprises recording computed tomography images for a number of irradiation sessions,
   wherein reconstructing the dose administered to the object comprises reconstructing the dose administered for each of the irradiation sessions using the computed tomography image recorded in the irradiation session, and
   wherein the method further comprises determining an applied dose cumulated during the course of the irradiation sessions for a structure in the object.

6. The method as claimed in claim 2, further comprising:
   rotating the portal detector about a center of rotation; and
   assigning the measurement data recorded by the portal detector to rotation positions, at which the recording of the measurement data has taken place,
   wherein reconstructing the dose administered to the object comprises reconstructing the dose administered to the object using the rotation positions assigned to the measurement data.

7. The method as claimed in claim 2, wherein the computed tomography image is the only three dimensional (3D) image of the object that is used during the reconstruction of the dose administered to the object.

8. The method as claimed in claim 3, wherein the computed tomography image is the only three dimensional (3D) image of the object that is used during the reconstruction of the dose administered to the object.

9. The method as claimed in claim 2, wherein recording the computed tomography image comprises recording computed tomography images for a number of irradiation sessions,
   wherein reconstructing the dose administered to the object comprises reconstructing the dose administered for each of the irradiation sessions using the computed tomography image recorded in the irradiation session, and
   wherein the method further comprises determining an applied dose cumulated during the course of the irradiation sessions for a structure in the object.

10. The method as claimed in claim 3, wherein recording the computed tomography image comprises recording computed tomography images for a number of irradiation sessions,
    wherein reconstructing the dose administered to the object comprises reconstructing the dose administered for each of the irradiation sessions using the computed tomography image recorded in the irradiation session, and
    wherein the method further comprises determining an applied dose cumulated during the course of the irradiation sessions for a structure in the object.

11. The method as claimed in claim 4, wherein recording the computed tomography image comprises recording computed tomography images for a number of irradiation sessions,
    wherein reconstructing the dose administered to the object comprises reconstructing the dose administered for each of the irradiation sessions using the computed tomography image recorded in the irradiation session, and
    wherein the method further comprises determining an applied dose cumulated during the course of the irradiation sessions for a structure in the object.

12. A radiation therapy device for treatment of an object to be treated and for reconstruction of a dose administered to the object to be irradiated during the treatment, the radiation therapy device comprising:
  a therapeutic radiation source operable to emit a therapeutic treatment beam;
  a portal detector opposing the therapeutic radiation source, the portal detector operable to record measurement data of the therapeutic treatment beam once the therapeutic treatment beam has left the object to be irradiated, the measurement data including portal images recorded during treatment;
  a single or multi slice computed tomography scanner comprising a kV x-ray source and an opposing kV detector operable for producing a computed tomography of the object positioned in the radiation therapy device; and
  a control apparatus configured to:
    record a computed tomography image of the object to be irradiated with the single or multi slice computed tomography scanner during a treatment session; and
    reconstruct the dose administered to the object from the portal images recorded during treatment and the recorded computed tomography image, wherein the reconstruction comprises:
      conversion of the portal images to energy fluences; and
      backprojection of the energy fluences using the computed tomography image as a model.

13. The radiation therapy device as claimed in claim 12, wherein the control apparatus is further configured to:
  convert the measurement data of the portal detector into dose in water/dose to water values; and
  reconstruct the dose administered to the object from the dose in water/dose to water values using the computed tomography image.

14. The radiation therapy device as claimed in claim 12, wherein the portal detector is rotatable about a center of rotation; and
  wherein the control apparatus is further configured to:
    assign a rotation position, at which the measurement data has been recorded in each instance, to the measurement data recorded by the portal detector; and
    reconstruct the dose administered to the object using the rotation position assigned to the measurement data in each instance.

15. The radiation therapy device as claimed in claim 12, wherein the control apparatus is further configured such that during the reconstruction of the dose administered to the object, the computed tomography image is the only image of the object that is used.

16. The radiation therapy device as claimed in claim 12, wherein the control apparatus is further configured to:
  record computed tomography images in a number of irradiation sessions; and
  implement a reconstruction of the dose administered for each of the irradiation sessions using the computed tomography image recorded in the irradiation session; and
  determine an applied dose cumulated during the course of the irradiation sessions for a structure in the object.

17. The radiation therapy device as claimed in claim 13, wherein the portal detector is rotatable about a center of rotation; and
  wherein the control apparatus is further configured to:
    assign a rotation position, at which the measurement data has been recorded in each instance, to the measurement data recorded by the portal detector; and
    reconstruct the dose administered to the object using the rotation position assigned to the measurement data in each instance.

18. The radiation therapy device as claimed in claim 13, wherein the control apparatus is further configured such that during the reconstruction of the dose administered to the object, the computed tomography image is the only image of the object that is used.

19. The radiation therapy device as claimed in claim 14, wherein the control apparatus is further configured such that during the reconstruction of the dose administered to the object, the computed tomography image is the only image of the object that is used.

20. The radiation therapy device as claimed in claim 13, wherein the control apparatus is further configured to:
  record computed tomography images in a number of irradiation sessions; and
  implement a reconstruction of the dose administered for each of the irradiation sessions using the computed tomography image recorded in the irradiation session; and
  determine an applied dose cumulated during the course of the irradiation sessions for a structure in the object.

* * * * *